United States Patent [19]

Bundy

[11] 4,089,878
[45] May 16, 1978

[54] ω-ARYL-9-DEOXY-PGF COMPOUNDS

[75] Inventor: Gordon L. Bundy, Portage, Mich.

[73] Assignee: The Upjohn Company, Kalamazoo, Mich.

[21] Appl. No.: 786,709

[22] Filed: Apr. 11, 1977

Related U.S. Application Data

[62] Division of Ser. No. 614,243, Sep. 17, 1975, Pat. No. 4,033,989.

[51] Int. Cl.² .......................................... C07C 177/00
[52] U.S. Cl. ..................... 260/408; 260/410; 260/410.5; 260/410.9 R; 260/413; 260/520 R; 560/55
[58] Field of Search .................. 260/408, 410, 410.5, 260/413, 520 R; 560/55

[56] References Cited

U.S. PATENT DOCUMENTS 3,678,092  7/1972  Finch .................................. 560/121

FOREIGN PATENT DOCUMENTS 767,704  11/1971  Belgium ............................... 560/121

*Primary Examiner*—Paul J. Killos
*Attorney, Agent, or Firm*—Robert A. Armitage

[57] ABSTRACT

Prostaglandin analogs with the following cyclopentane ring structure:

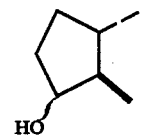

are disclosed along with intermediates useful in their preparation and processes for their preparation. These analogs are useful for some of the same pharmacological purposes as the prostaglandins.

8 Claims, No Drawings

ω-ARYL-9-DEOXY-PGF COMPOUNDS

The present application is a divisional application of Ser. No. 614,243, filed Sept. 17, 1975, now issued as U.S. Pat. 4,033,989 on July 5, 1977.

The present invention relates to prostaglandin analogs for which the essential material constituting a disclosure therefor is incorporated by reference here from U.S. Pat. No. 4,033,989, issued July 5, 1977.

I claim:

1. A prostaglandin analog of the formula $$D\underset{Y-\underset{M_1}{\overset{\parallel}{C}}-\underset{L_1}{\overset{\parallel}{C}}-Z_3-}{\overset{CH_2-Z_1-COOR_1}{\diagup}} \diagdown \phantom{x} (T)_s$$

wherein D is

[cyclopentane structure with HO and methyl substituents]

or

[cyclopentane structure with HO and methyl substituents];

wherein Y is cis—CH=CH—, trans—CH=CH—, or —CH$_2$CH$_2$—;

wherein M$_1$ is $$R_5\diagup\diagdown OR_6$$

or $$R_5\diagup\diagdown OR_6,$$

wherein R$_5$ and R$_6$ are hydrogen or methyl, with the proviso that one of R$_5$ and R$_6$ is methyl only when the other is hydrogen;

wherein L$_1$ is $$R_3\diagup\diagdown R_4,$$

$$R_3\diagup\diagdown R_4,$$

or a mixture of $$R_3\diagup\diagdown R_4$$

and $$R_3\diagup\diagdown R_4,$$

wherein R$_3$ and R$_4$ are hydrogen, methyl, or fluoro, being the same or different, with the provisio that one of R$_3$ and R$_4$ is hydrogen or fluoro only when the other is hydrogen or fluoro;

wherein Z$_3$ is oxa of methylene;

wherein [m is one to 5, inclusive,] T is chloro, fluoro, trifluoromethyl, alkyl, of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that [R$_7$ is ] Z$_3$ is oxa only when R$_3$ and R$_4$ are hydrogen or methyl, being the same or different;

wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of one to 3 carbon atoms, inclusive, or a pharmacologically acceptable cation;

wherein Z$_1$ is (1) cis—CH=CH—CH$_2$—(CH$_2$)$_g$—CF$_2$—,
(2) cis—CH=CH—CH$_2$—(CH$_2$)$_g$—CH$_2$—,
(3) cis—CH$_2$—CH=CH—(CH$_2$)$_g$—CH$_2$—,
(4) —(CH$_2$)$_3$—(CH$_2$)$_g$—CF$_2$—,
(5) —(CH$_2$)$_3$—(CH$_2$)$_g$—CH$_2$—,
(6) —CH$_2$—O—CH$_2$—(CH$_2$)$_g$—CH$_2$—,
(7) —(CH$_2$)$_2$—O—(CH$_2$)$_g$—CH$_2$—,
(8) —(CH$_2$)$_3$—O—(CH$_2$)$_g$—,

[phenyl group]—CH$_2$—(CH$_2$)$_g$—, (9)

or

[phenyl group]—O—(CH$_2$)$_g$— (10)

wherein g is one, 2, or 3.

2. A compound according to claim 1, wherein D is

[cyclopentane structure with HO and methyl substituents]

3. A compound according to claim 1, wherein D is

4. A compound according to claim 3, wherein M₁ is
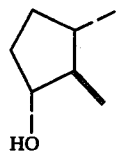
5. A compound according to claim 3, wherein M₁ is
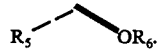
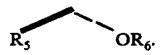
6. A compound according to claim 5, wherein Y is cis—CH=CH—.
7. A compound according to claim 5, wherein Y is —CH₂CH₂—.
8. A compound according to claim 5, wherein Y is trans—CH=CH—.
* * * * *

UNITED STATES PATENT OFFICE
CERTIFICATE OF CORRECTION

Patent No. 4,089,878    Dated    May 16, 1978

Inventor(s)    Gordon L. Bundy

It is certified that error appears in the above-identified patent and that said Letters Patent are hereby corrected as shown below:

Column 2, line 17, "wherein [m is one to 5, inclusive,] T is chloro, fluoro," should read -- wherein T is chloro, fluoro, --; lines 22-23, "that [$R_7$ is] $Z_3$ is oxa" should read -- that $Z_3$ is oxa -- .

Signed and Sealed this

*Twenty-fourth* Day of *October 1978*

[SEAL]

*Attest:*

RUTH C. MASON
*Attesting Officer*

DONALD W. BANNER
*Commissioner of Patents and Trademarks*